(12) United States Patent
Sims et al.

(10) Patent No.: US 6,796,975 B2
(45) Date of Patent: Sep. 28, 2004

(54) CONTAINER FOR LINEZOLID INTRAVENOUS SOLUTION

(75) Inventors: Sandra M. Sims, Portage, MI (US); Phil Bryan Bowman, Kalamazoo, MI (US); Daniel C. Wade, Portage, MI (US); Shri C. Valvani, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 449 days.

(21) Appl. No.: 09/809,695

(22) Filed: Mar. 15, 2001

(65) Prior Publication Data

US 2001/0049383 A1 Dec. 6, 2001

Related U.S. Application Data

(60) Provisional application No. 60/191,383, filed on Mar. 22, 2000.

(51) Int. Cl.[7] ............................................. A61B 19/00
(52) U.S. Cl. ..................................................... 604/403
(58) Field of Search ...................... 260/42.42; 428/35.7; 514/818, 376, 233.8, 236.8, 235.8, 235.5, 312; 544/137; 604/403

(56) References Cited

U.S. PATENT DOCUMENTS

| | | | |
|---|---|---|---|
| 3,997,494 A | * 12/1976 | Lever et al. .............. 260/42.42 |
| 5,114,765 A | * 5/1992 | Inada et al. ................. 428/35.7 |
| 5,529,998 A | 6/1996 | Habich et al. ............ 514/233.8 |
| 5,547,950 A | 8/1996 | Hutchinson et al. ........ 514/252 |
| 5,627,181 A | 5/1997 | Riedl et al. .............. 514/236.8 |
| 5,684,023 A | 11/1997 | Riedl et al. .................. 514/337 |
| 5,688,791 A | 11/1997 | Kimura .................... 514/224.5 |
| 5,688,792 A | 11/1997 | Barbachyn ............... 514/235.5 |
| 5,698,574 A | 12/1997 | Riedl et al. .................. 514/376 |
| 5,700,799 A | 12/1997 | Hutchinson et al. ...... 514/235.8 |
| 5,792,765 A | 8/1998 | Riedl et al. ............... 514/236.8 |
| 5,827,857 A | 10/1998 | Riedl et al. .................. 514/301 |
| 5,837,870 A | 11/1998 | Pearlman et al. ............ 544/137 |
| 5,843,967 A | 12/1998 | Riedl et al. .................. 514/340 |
| 5,861,413 A | 1/1999 | Habich et al. ............... 514/312 |
| 5,869,659 A | 2/1999 | Stolle et al. ................. 544/114 |
| 5,968,962 A | 10/1999 | Thomas et al. ............. 514/376 |
| 6,284,805 B1 | * 9/2001 | Brown ........................ 514/818 |

FOREIGN PATENT DOCUMENTS

| EP | 0 067 420 A1 | 12/1982 | ........... B65B/55/02 |
| WO | WO 99/24393 | 5/1999 | ......... C07C/233/16 |
| WO | WO 01/34128 A2 | 5/2001 | .......... A61K/31/00 |

OTHER PUBLICATIONS

J. F. Carley, *Whittington's Dictionary of Plastics*, Technomic Publishing Company, Inc., 1993, 387.

* cited by examiner

*Primary Examiner*—Henry Bennett
*Assistant Examiner*—Sabrina Dagostino
(74) *Attorney, Agent, or Firm*—Stephen L. Nesbitt; Bruce Stein

(57) ABSTRACT

The present invention is a container for an IV aqueous solution of a Gram-positive oxazolidinone agent, such as linezolid a the compound of formula:

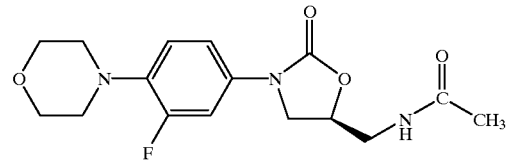

which comprises having the container-solution contact surface material be a polyolefin.

16 Claims, No Drawings

US 6,796,975 B2

CONTAINER FOR LINEZOLID INTRAVENOUS SOLUTION

CROSS-REFERENCE TO RELATED APPLICATIONS

This application claims the benefit of the following provisional application: U.S. Ser. No. 60/191,383, filed Mar. 22, 2000, under USC 119(e)(i).

BACKGROUND OF THE INVENTION

1. Field of the Invention

The invention is the use of polyolefins as the material in IV containers which is in contact with pharmaceutically useful antibacterial oxazolidinone agents during and after moist heat sterilization.

2. Description of the Related Art

Oxazolidinones are well known to those skilled in the art as gram positive anti-bacterial agents, see, for example, U.S. Pat. Nos. 5,688,792, 5,529,998, 5,547,950, 5,627,181, 5,700,799, 5,843,967, 5,792,765, 5,684,023, 5,861,413, 5,827,857, 5,869,659, 5,698,574, 5,968,962 and 5,981,528.

Various containers are known to hold aqueous solutions to be administered IV to a patient. The most common IV solution containers are glass and plastic bottles and plastic bags U.S. Pat. No. 4,803,102 discloses containers for IV solutions where the material in contact with the aqueous solution to be administered IV is made primarily of polyolefin(s).

SUMMARY OF INVENTION

Disclosed is a container for an IV aqueous solution of a Gram-positive oxazolidinone agent which comprises having the container-solution contact surface material is made of at least 50% polyolefin.

Also disclosed is a method of preventing loss of a Gram-positive oxazolidinone agent during and following terminal sterilization with moist heat in an IV aqueous solution to be terminal sterilized with moist heat which comprises:

(1) placing the IV aqueous solution in a container to be sterilized where the container-solution contact surface material is made of at least 50% polyolefin and (2) moist heat sterilizing the container-solution.

DETAILED DESCRIPTION OF THE INVENTION

Oxazolidinones are a new class of Gram-positive antibacterial agents which are known to those skilled in the art, see for example U.S. Pat. No. 5,688,792. (S)-N-[[3-[3-fluoro-4-(4-morpholinyl)phenyl]-2-oxo-5-oxazolidinyl]methyl]acetamide, known as linezolid, the compound of Example 5 of U.S. Pat. No. 5,688,792 is known and has the following chemical formula:

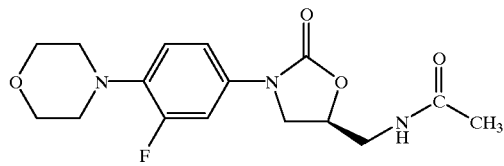

(S)-N-[[3-[3-fluoro-4-[4-(hydroxyacetyl)-1-piperazinyl]-phenyl]-2-oxo-5-oxazolidinyl]methyl]acetamide, known as eperezolid, the compound of Example 8 of U.S. Pat. No. 5,837,870 is known and has the following chemical formula:

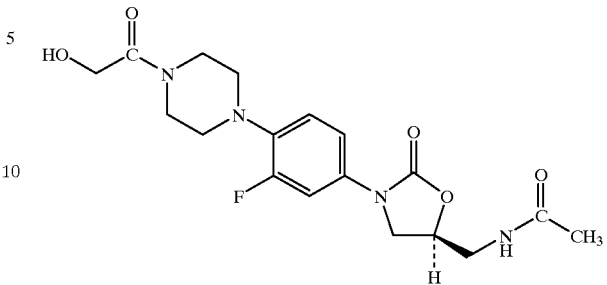

Linezolid and eperezolid can be produced by the processes set forth in U.S. Pat. Nos. 5,688,791 and 5,837,870 as well as that of International Publication WO99/24393. It is preferably produced by the process of U.S. Pat. No. 5,837,870.

It is preferred that the linezolid produced be used in crystal form II, which has the characteristics set forth in CHART A. Once linezolid is synthesized, crystal Form II is prepared by starting with linezolid of high enantiomeric purity. It is preferred that the linezolid be more than 98% enantiomerically pure, it is more preferred that the linezolid be more than 99% pure and it is even more preferred that the linezolid be 99.5% pure. The linezolid of greater than 98% enantiomeric purity to be used to form crystal form II can either be in solution or be a solid. The linezolid starting material, solid or solution, is mixed with a solvent selected from the group consisting of compounds of the formula: water, acetonitrile, chloroform, methylene chloride, $R_1$—OH where $R_1$ is $C_1$–$C_6$ alkyl; $R_1$—CO—$R_2$ where $R_2$ is $C_1$–$C_6$ alkyl and $R_1$ is as defined above; phenyl substituted with 1 thru 3 $R_1$ where $R_1$ is as defined above; $R_1$—CO—O—$R_2$ where $R_1$ is $C_1$–$C_6$ alkyl and $R_1$ is as defined above; $R_1$—O—$R_2$ where $R_1$ is $C_1$–$C_6$ alkyl and $R_1$ is as defined above. It is preferred that the solvent be selected from the group consisting of water, ethyl acetate, methanol, ethanol, propanol, isopropanol, butanol, acetonitrile, acetone, methyl ethyl ketone, chloroform, methylene chloride, toluene, xylene, diethyl ether, or methyl-t-butyl ether. It is more preferred that the solvent be ethyl acetate, acetone, acetonitrile, propanol, or isopropanol. It is most preferred that the solvent be ethyl acetate. The mixture of linezolid in the solvent is agitated at a temperature below 80° until crystals of Form II are formed and crystals of other solid forms, such as Form I, disappear. It is preferred to dissolve the linezolid in ethyl acetate at a temperature near the boiling point of the solvent. This mixture is cooled to a temperature of about 70°. The mixture may be seeded with crystals of Form II to facilitate crystallization. It is preferred that the solid product is cooled and agitated at a temperature between about 45° and about 60° until the solids consist only of Form II crystals. It is most preferred to maintain the slurry at a temperature of about 55°. It is preferred to mix the linezolid and solvent for at least 10 min, it is even more preferred to mix the linezolid and solvent for at least 20 min and it is most preferred to mix the linezolid and solvent for at least 30 min. The time and temperature will vary depending on the solvent selected. With ethyl acetate it is preferred to mix for not less that 60 minutes. The crystalline slurry may be further cooled to improve yield, and the solid Form II product may be isolated. The mixture may be further cooled and agitated. Other measures which can be used to facilitate crystallization include, but are not limited to, cooling, concentration of the solution by evaporation or distillation, or through addition of other solvents. The crystals are isolated by procedures known to those skilled in the art.

It is well known to those skilled in the art that the oxazolidinones are useful as anti-bacterial agents especially against Gram-positive organisms. U.S. Pat. No. 5,688,792 discloses that oxazolidinones can be administered IV. The preferred formulation for linezolid IV solution is:

| | |
|---|---|
| Linezolid | 2.0 mg/mL |
| Sodium Citrate Dihydrate (USP) | 1.64 mg/mL |
| Citric Acid Anhydrous (USP) | 0.85 mg/mL |
| Dextrose Monohydrate (USP) | 50.24 mg/mL |
| Hydrochloric Acid (10%) q.s. to pH 4.8 (pH 4.6 to 5.0) | |
| Sodium hydroxide (10%) q.s. to pH 4.8 (pH 4.6 to 5.0) | |
| Water for Injection (USP) | q.s. ad 1.0 mL |

The linezolid IV solution is formulated by heating water for injection from about 50 to about 65°. Next the sodium citrate, citric acid and dextrose are added and stirred until dissolved. An aqueous slurry of linezolid is added to the previous mixture and stirred until dissolved. The mixture is cooled to 25° with stirring. The pH is measured and adjusted if necessary. Last the mixture is brought to volume, if necessary, with water for injection. The mixture is filtered, filled into infusion containers, over wrapped and terminally moist heat sterilized.

The aqueous solution for IV administration can be placed in the container which is selected from the group consisting of a bag, a bottle, a vial, a large volume parenteral, a small volume parenteral, a prefilled syringe and a cassette. It is realized that a vial is a bottle. However, those skilled in the art use the term "bottle" to refers to larger bottles and "vials" to refer to smaller bottles. It is preferred that the container be a bag, a bottle, a vial or a prefilled syringe. It is more preferred that the container be a bag or bottle. It is most preferred that the container be a bag. The shape and/or size of the container is unimportant. It is preferred that the container be a bag sufficient to hold 25 to 2,000 mL of IV solution. It is preferred that the linezolid mixture be put in bags in amounts of 100, 200 or 300 mL of solution however smaller or larger volumes are acceptable.

It is well known to those skilled in the art that pharmaceutical agents administered IV must be sterile. While there are a number of methods to sterilize an IV solution, it is preferred to terminally moist heat or steam sterilize IV solutions of oxazolidinones including those of linezolid. When the term terminally "moist heat sterilize" is used, it refers to and includes steam sterilization.

When terminally moist heat sterilizing an IV solution, the solution is placed in the container in which (1) it will be stored and then transferred to the container from which it will ultimately be administered, or (2) stored and then ultimately administered from the same container to deliver the IV solution to the patient. Therefore, it is imperative that the pharmaceutically active ingredient (oxazolidinone, linezolid) not react with the container in which it is to be terminally moist heat sterilized and stored/stored-administered.

It has been found that when the container-solution contact surface is made of at least 50% polyolefin there is significantly much less loss of linezolid during and following terminal moist heat sterilization. What is essential is that the container-solution contact surface material be primarily a polyolefin; the remainder of the container can be made from polyolefin or other materials. It is preferred that the container-solution contact surface is made of from about 50 to about 100% polyolefin. It is more preferred that the container-solution contact surface is made of from about 70 to about 90% polyolefin. It is more preferred that the container-solution contact surface is made of from about 80% polyolefin. It is even more preferred that the container-solution contact surface is made of polyolefin.

Polyolefins include, for example, polyethylene, polypropylene, polybutenes, polyisoprenes and polypentenes and copolymers and mixtures thereof. It is preferred that the polyolefin be selected from the group consisting of polyethylene and polypropylene. It is more preferred that the polyolefin be polypropylene or mixture of polypropylene and polyethylene.

DEFINITIONS AND CONVENTIONS

The definitions and explanations below are for the terms as used throughout this entire document including both the specification and the claims.

DEFINITIONS

Linezolid refers to (S)-N-[[3-[3-fluoro-4-(4-morpholinyl) phenyl]-2-oxo-5-oxazolidinyl]methyl]acetamide is the compound of formula:

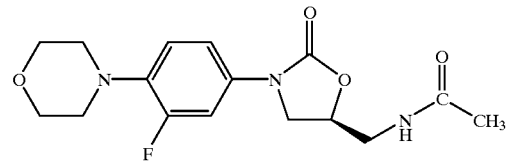

Eperezolid refers to (S)-N-[[3-[3-fluoro-4-[4-(hydroxyacetyl)-1-piperazinyl]-phenyl]-2-oxo-5-oxazolidinyl]methyl]acetamide is the compound of formula:

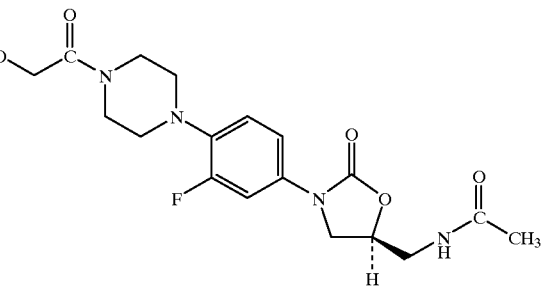

All temperatures are in degrees Celsius.

Polyolefins (as defined in Whittington's Dictionary of Plastics, James F. Carley, Ed., Technomic Publishing Co., Lancaster, Pa., 1993) refers to any of the largest genus of thermoplastics, polymers of simple olefins such as ethylene, propylene, butenes, isoprenes, and pentenes and copolymers and modifications thereof.

IV refers to intravenous.

"Heat sterilize" and "moist heat sterilize" refers to and includes steam sterilization.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

Linezolid IV Solution (1 mL)

The composition of Linezolid IV solution is as follows:

| | |
|---|---|
| Linezolid | 2.0 mg |
| Dextrose, USP | 50.24 mg |
| Sodium citrate, USP | 1.64 mg |
| Citric acid, USP | 0.85 mg |
| Water for injection, USP | q.s. ad 1 ml |

The linezolid IV solution is formulated by heating water for injection to 60°. Next the sodium citrate, citric acid and dextrose are added and stirred until dissolved. An aqueous slurry of linezolid is added to the previous mixture and stirred until dissolved. The mixture is cooled to 25° with stirring. The pH is measured and adjusted if necessary. Last the mixture is brought to volume, if necessary with water for injection. The mixture is filtered, filled into infusion containers, over wrapped and terminally moist heat sterilized.

Example 2

Linezolid IV Solution (300 mL)

Following the general procedure of EXAMPLE 1 and making non-critical variations but using 300 times the amount of each ingredient, 600 mg of linezolid, the title IV solution is prepared.

Chart A

Linezolid, (S)-N-[[3-[3-fluoro-4-(4-morpholinyl)phenyl]-2-oxo-5-oxazolidinyl]methyl]acetamide, crystal "Form II" has the powder X-ray diffraction spectrum of:

| d-Spacing (Å) | Two-Theta Angle (°) | Relative Intensity (%) |
|---|---|---|
| 12.44 | 7.10 | 2 |
| 9.26 | 9.54 | 9 |
| 6.37 | 13.88 | 6 |
| 6.22 | 14.23 | 24 |
| 5.48 | 16.18 | 3 |
| 5.28 | 16.79 | 100 |
| 5.01 | 17.69 | 2 |
| 4.57 | 19.41 | 4 |
| 4.50 | 19.69 | 2 |
| 4.45 | 19.93 | 6 |
| 4.11 | 21.61 | 15 |
| 3.97 | 22.39 | 23 |
| 3.89 | 22.84 | 4 |
| 3.78 | 23.52 | 7 |
| 3.68 | 24.16 | 1 |
| 3.52 | 25.28 | 13 |
| 3.34 | 26.66 | 1 |
| 3.30 | 27.01 | 3 |
| 3.21 | 27.77 | 1 | and an infrared (IR) spectrum (mineral oil mull) of 3364, 1748, 1675, 1537, 1517, 1445, 1410, 1401, 1358, 1329, 1287, 1274, 1253, 1237, 1221, 1145, 1130, 1123, 1116, 1078, 1066, 1049, 907, 852 and 758 $cm^{-1}$.

What is claimed is:

1. A container for an IV aqueous solution of a Gram-positive oxazolidinone agent selected from the group consisting of linezolid and eperezolid which comprises having the container-solution contact surface material is made of at least 50% polyolefin.

2. A container for an IV aqueous solution according to claim 1 where the container is selected from the group consisting of a bag, a bottle, a vial, a large volume parenteral, a small volume parenteral, a prefilled syringe and a cassette.

3. A container for an IV aqueous solution according to claim 2 where the container is a bag, a bottle, a vial and a prefilled syringe.

4. A container for an IV aqueous solution according to claim 2 where the container is a bag.

5. A container for an IV aqueous solution according to claim 2 where the container is a bottle.

6. A container for an IV aqueous solution according to claim 2 where the container is a vial.

7. A container for an IV aqueous solution according to claim 2 where the container is a prefilled syringe.

8. A container for an IV aqueous solution according to claim 1 where the container-solution contact surface is made of polyolefin or made primarily of polyolefin.

9. A container for an IV aqueous solution according to claim 8 where the container-solution contact surface is made of from about 50 to about 100% polyolefin.

10. A container for an IV aqueous solution according to claim 9 where the container-solution contact surface is made of from about 70 to about 90% polyolefin.

11. A container for an IV aqueous solution according to claim 10 where the container-solution contact surface is made of from about 80% polyolefin.

12. A container for an IV aqueous solution according to claim 1 where the container-solution contact surface is made of polyolefin.

13. A container for an IV aqueous solution according to claim 1 where the polyolefin is selected from the group consisting of polyethylene, polypropylene, polybutenes, polyisoprenes and polypentenes and copolymers and mixtures thereof.

14. A container for an IV aqueous solution according to claim 13 where the polyolefin is selected from the group consisting of polyethylene and polypropylene.

15. A container for an IV aqueous solution according to claim 14 where the polyolefin is polypropylene.

16. A container for an IV aqueous solution according to claim 1 where the Gram-positive oxazolidinone agent is linezolid.

* * * * *